US011849912B2

(12) United States Patent
Zhang

(10) Patent No.: US 11,849,912 B2
(45) Date of Patent: Dec. 26, 2023

(54) ENDOSCOPIC CAMERA SYSTEM AND IMAGE SIGNAL TRANSMISSION METHOD THEREOF

(71) Applicant: SCIVITA MEDICAL TECHNOLOGY CO., LTD., Jiangsu (CN)

(72) Inventor: Yi Zhang, Suzhou (CN)

(73) Assignee: SCIVITA MEDICAL TECHNOLOGY CO., LTD., Suzhou (CN)

( * ) Notice: Subject to any disclaimer, the term of this patent is extended or adjusted under 35 U.S.C. 154(b) by 394 days.

(21) Appl. No.: 17/293,831

(22) PCT Filed: Jun. 13, 2019

(86) PCT No.: PCT/CN2019/091128
§ 371 (c)(1),
(2) Date: Jul. 21, 2021

(87) PCT Pub. No.: WO2020/103436
PCT Pub. Date: May 28, 2020

(65) Prior Publication Data
US 2022/0014660 A1    Jan. 13, 2022

(30) Foreign Application Priority Data
Nov. 19, 2018 (CN) .......................... 201811378392.X

(51) Int. Cl.
*A61B 1/00* (2006.01)
*G06F 11/07* (2006.01)
(Continued)

(52) U.S. Cl.
CPC ...... *A61B 1/000095* (2022.02); *A61B 1/0002* (2013.01); *A61B 1/00045* (2013.01);
(Continued)

(58) Field of Classification Search
CPC .......... A61B 1/000095; A61B 1/00043; A61B 1/0002; A61B 1/00045; A61B 1/045;
(Continued)

(56) References Cited

U.S. PATENT DOCUMENTS 6,638,212 B1 * 10/2003 Oshima ................. A61B 1/045
600/110
8,988,515 B2 * 3/2015 Takahashi .......... A61B 1/00018
600/109
(Continued)

FOREIGN PATENT DOCUMENTS

CN       102469928 A      5/2012
CN       103815859 A      5/2014
(Continued)

OTHER PUBLICATIONS

International Search Report and Written opinion issued for PCT/CN2019/091128 dated Aug. 28, 2019; 7 pages.

*Primary Examiner* — Brian P Yenke
(74) *Attorney, Agent, or Firm* — Reising Ethington P.C.

(57) ABSTRACT

An endoscope camera system and an image signal transmission method thereof are aimed at resolving a problem that an existing endoscope camera system cannot ensure a normal image output. The system may include a camera module, an image processing module, a front panel function switching module, a front panel control module, and a plurality of signal forwarding modules; when image signal transmission between an external monitor and the image processing module is abnormal, a signal forwarding module m is configured as a signal forwarding station that is used for bridging the image signal transmission between the image processing module and the external monitor. After receiving an image signal, the signal forwarding module m reprocesses the image signal and continues to send the image signal to the external monitor, thereby effectively avoiding (Continued)

signal attenuation and signal interference during the image signal transmission, and achieving an effect of ensuring a normal image output.

10 Claims, 7 Drawing Sheets

(51) Int. Cl.
| | |
|---|---|
| A61B 1/045 | (2006.01) |
| H04L 67/568 | (2022.01) |
| H04N 23/53 | (2023.01) |
| H04N 23/72 | (2023.01) |
| H04N 23/88 | (2023.01) |
| H04N 23/50 | (2023.01) |

(52) U.S. Cl.
CPC ............ *A61B 1/045* (2013.01); *H04L 67/568* (2022.05); *H04N 23/53* (2023.01); *H04N 23/72* (2023.01); *H04N 23/88* (2023.01); H04N 23/555 (2023.01)

(58) Field of Classification Search
CPC ..... H04L 67/586; H04L 67/568; H04N 23/53; H04N 23/72; H04N 23/88; H04N 23/555; G06F 11/073; G11B 2020/10629; G11B 2020/10657
See application file for complete search history.

(56) References Cited

U.S. PATENT DOCUMENTS

| | | | |
|---|---|---|---|
| 9,936,864 B2* | 4/2018 | Tsutsui | H04N 25/60 |
| 10,531,026 B2* | 1/2020 | Tsutsui | A61B 1/00006 |
| 11,045,072 B2* | 6/2021 | Okawa | A61B 1/045 |
| 2016/0316995 A1* | 11/2016 | Michihata | A61B 1/00117 |
| 2017/0006271 A1* | 1/2017 | Koizumi | G06T 5/001 |
| 2017/0237937 A1* | 8/2017 | Motohashi | H04N 23/90 |
| | | | 348/148 |
| 2017/0270263 A1* | 9/2017 | Michihata | G16H 30/20 |
| 2017/0339362 A1 | 11/2017 | Koyama | |
| 2018/0070797 A1* | 3/2018 | Fujita | A61B 1/00009 |
| 2018/0116486 A1* | 5/2018 | Mizukami | A61B 1/0002 |
| 2019/0269298 A1* | 9/2019 | Kiba | G16H 40/63 |
| 2021/0307587 A1* | 10/2021 | Iwasaki | A61B 1/0655 |

FOREIGN PATENT DOCUMENTS

| | | |
|---|---|---|
| CN | 104271027 A | 1/2015 |
| CN | 107529970 A | 1/2018 |
| CN | 109222854 A | 1/2019 |

* cited by examiner

ENDOSCOPIC CAMERA SYSTEM AND IMAGE SIGNAL TRANSMISSION METHOD THEREOF

FIELD

The present disclosure relates to the technical field of endoscope camera, and in particular, to an endoscope camera system and an image signal transmission method thereof.

BACKGROUND

In an endoscope camera system, sometimes an endoscope may be used in close proximity to a high-output electric knife depending on usage conditions thereof. Under such a condition of using the endoscope in close proximity to the high-output electric knife or the like, a driving pulse that drives a CMOS sensor is easily affected by noise from the electric knife, and there are cases in which set data is rewritten as an illegal value when the set data is transferred from a processor side, or the set data kept in a register disappears because a power source of an imaging portion including the register is cut off. Thus, the endoscope of the CMOS sensor sometimes cannot ensure a normal image output.

To resolve the foregoing problem, various solutions for making sure that an endoscope system normally outputs an image are also proposed in the prior art. For example:

A camera device and an endoscope system disclosed in the Chinese patent publication No. CN103200859A, filed on 2 Jul. 2012 by Olympus Corporation include: a sensor portion, which photographs a photographed object; a control register portion, which controls the sensor portion; a nonvolatile memory, which stores set data that is set for the control register portion; a control signal interface portion, which sets the set data that is stored in the nonvolatile memory to the control register portion; and an initialization confirming register, which detects an exception of the control register portion. The control signal interface portion reads the set data from the nonvolatile memory when the initialization confirming register detects an exception, so as to control to reset the control register portion.

According to the foregoing existing technical solution, the control register portion is reset by reading the set data from the nonvolatile memory only when the control register portion is detected to be abnormal, so as to ensure a normal image output. However, when the endoscope system transmits an image signal to a display device (such as an external monitor, the external monitor may be a monitor used by a doctor for observing, or may be a monitor outside an operation room for a trainee to view), a picture displayed by the display device may easily have problems such as bad pixels, noise, blurring, and blinking due to signal interference caused by signal attenuation or noise. In other words, the display device cannot normally output an image.

SUMMARY

Objectives of the present disclosure are to provide an endoscope camera system and an image signal transmission method thereof.

Objective I is to provide an endoscope camera system that can ensure a normal image output.

Objective II is to provide an image signal transmission method for an endoscope camera system that can ensure a normal image output.

The foregoing objective I of the present disclosure may be achieved through the following technical solutions.

An endoscope camera system, including:
- a camera module, configured to convert an optical signal to an electrical signal, and process the electrical signal as an image signal to output;
- an image processing module, connected to the camera module and configured to reprocess the image signal output by the camera module and then output the same to an external monitor;
- a front panel function switching module, configured to be operated by a user and to send a control signal for switching image processing functions to the image processing module based on an operation of the user;
- a front panel control module, connected to the image processing module and the front panel function switching module, and configured to enable the front panel function switching module to communicate with the image processing module; and
- a plurality of signal forwarding modules, each of the signal forwarding modules being directly connected to a line through which the image processing module and the external monitor are connected, where
- when image signal transmission between the external monitor and the image processing module is abnormal, a signal forwarding module m is configured as a signal forwarding station that is used for bridging the image signal transmission between the image processing module and the external monitor, and the signal forwarding module m is any one of the plurality of signal forwarding modules.

According to the foregoing technical solution, when the image signal transmission between the external monitor and the image processing module is abnormal, the system may configure a signal forwarding module to serve as the signal forwarding station that is used for bridging the image signal transmission between the image processing module and the external monitor. When the image signal transmission between the external monitor and the image processing module is still abnormal, the system continues to configure a signal forwarding station for the external monitor and the image processing module, until the image signal transmission between the external monitor and the image processing module is normal, thus effectively ensuring a normal image output.

The present disclosure may be further arranged so that the image processing module includes a white balance adjustment unit, a brightness adjustment unit, a wide dynamic functional unit, a dark place correction unit, an exposure correction unit, a smoke eliminating unit, a vessel enhancement unit, and a special camera unit.

According to the foregoing technical solution, the white balance adjustment unit is configured to adjust white balance of an output image; the brightness adjustment unit is configured to adjust image brightness; the wide dynamic functional unit has a function of dynamically expanding a range; the dark place correction unit is configured to improve brightness at a dark place of the image; the exposure correction unit can reduce excessive exposure; the smoke eliminating unit can eliminate smoke generated due to an operation in the image; the vessel enhancement unit can enhance color of a vessel in the image; and the special camera unit is configured to perform special imaging such as monochrome. Correspondingly, the front panel function switching module is provided with several function buttons or touch screens that correspond to various functional units in the image processing module, and the user can switch to a corresponding function by using the front panel function switching module.

The present disclosure may be further arranged so that the endoscope camera system further includes an image caching module connected to the image processing module, and the image caching module is configured to temporarily store an image input by the image processing module and output the temporarily stored image to an external storage device that is already connected.

According to the foregoing technical solution, after the external storage device is connected to the image caching module, the system can recognize automatically, to implement a function of synchronously storing an image. The external storage device stores the image once being connected.

The present disclosure may be further arranged so that the endoscope camera system further includes: a monitoring module, configured to detect quality of the image signal transmission between the image processing module and the external monitor; and a triggering module, configured to control the image processing module to send a start instruction to the signal forwarding module m when the monitoring module detects that the image signal transmission between the external monitor and the image processing module is abnormal.

According to the foregoing technical solution, the quality of the image signal transmission between the image processing module and the external monitor can be monitored in a real-time manner, thus effectively ensuring starting efficiency of the signal forwarding module m, so as to ensure normal image output efficiency.

The present disclosure may be further arranged so that the endoscope camera system further includes a signal caching module connected to the image processing module, the signal caching module includes: a storage unit, where the image processing module synchronously sends a same image signal to the storage unit and the external monitor, and the storage unit includes several consecutive storage regions that are used for storing the image signal; a numbering unit, configured to sequentially number the storage regions in the storage unit, and further configured to continuously move, when a storage region with a certain number is filled with image signals, the image signals in the storage region to a storage region with a previous number; an eliminating unit, configured to eliminate, when a storage region with a smallest number in the storage unit is filled with image signals, the image signals in the storage region; and a transmission unit, configured to copy, after the signal forwarding module m is started, the image signal in the storage unit and transmit the copied image signal to the signal forwarding module m, where the image processing module continuously transmits image signals to a storage region with a largest number in the storage unit, and the signal forwarding module m splices the image signal transmitted by the transmission unit and the image signal transmitted by the image processing module and then transmits the same to the external monitor.

According to the foregoing technical solution, historical image signals stored in the signal caching module can be seamlessly spiced with a real-time image signal transmitted by the image processing module, so that pictures of the external monitor are consecutive and complete.

The present disclosure may be further arranged so that: the monitoring module is configured to send normal data to the external monitor, the external monitor sends feedback information to the monitoring module after receiving the normal data, and the external monitor is further configured to send warning information to the monitoring module when the image signal received by the external monitor is distorted, where the triggering module is started if the monitoring module does not receive the corresponding feedback information or receives the warning information.

The foregoing objective II of the present disclosure may be achieved through the following technical solutions.

An image signal transmission method for an endoscope camera system, where the image signal transmission method is based on the foregoing endoscope camera system, and includes the following steps:

S10. establishing a data connection between the image processing module and the external monitor;

S20. converting, by the camera module, an optical signal to an electrical signal;

S30. processing, by the camera module, the converted electrical signal as an image signal and outputting the processed image signal to the image processing module;

S40. reprocessing, by the image processing module, the image signal input to the image processing module based on a function selected by the front panel function switching module, and outputting the reprocessed image signal to the external monitor and the signal caching module; and S50. detecting the quality of the image signal transmission between the image processing module and the external monitor, and when the image signal transmission between the image processing module and the external monitor is abnormal, configuring the signal forwarding module m as a signal forwarding station that is used for bridging a data connection between the image processing module and the external monitor, where the signal forwarding module m is any one of the plurality of signal forwarding modules.

According to the foregoing technical solution, when the image signal transmission between the external monitor and the image processing module is abnormal, the signal forwarding module m may be configured as a signal forwarding station for a data connection between the image processing module and the external monitor, so as to ensure quality of data transmission between the image processing module and the external monitor, thus effectively ensuring a normal image output.

The present disclosure may be further arranged so that the step S40 includes the following sub-steps:

S41. dividing internal storage space of the signal caching module into several consecutive storage regions;

S42. sequentially numbering the storage regions in the signal caching module;

S43. reprocessing, by the image processing module, the image signal input to the image processing module based on the function selected by the front panel function switching module;

S44. continuously transmitting, by the image processing module, the reprocessed image signal to the external monitor and a storage region with a largest number in the signal caching module; and S45. when a storage region with a certain number in the signal caching module is filled with image signal, continuously moving the image signal in the storage region to a storage region with a previous number, and when a storage region with a smallest number in the signal caching module is filled with image signal, eliminating the image signal in the storage region.

According to the foregoing technical solution, the image signal is cached, so that the cached image signal is transmitted to the signal forwarding module m when the signal transmission is abnormal, thus ensuring a normal image output.

The present disclosure may be further arranged so that the step S50 includes the following sub-steps:
- S51. detecting the quality of the image signal transmission between the image processing module and the external monitor;
- S52. when the image signal transmission between the image processing module and the external monitor is abnormal, configuring the signal forwarding module m as a signal forwarding station that is used for bridging a data connection between the image processing module and the external monitor;
- S53. copying, by the signal caching module, an image signal cached thereby and outputting the copied image signal to the signal forwarding module m; and
- S54. splicing, by the signal forwarding module m, the image signal output by the signal caching module and the image signal output by the image processing module and then outputting the same to the external monitor.

According to the foregoing technical solution, after receiving historical image signals transmitted by the signal caching module and a real-time image signal currently transmitted by the image processing module, the signal forwarding module m may seamlessly splice them, and perform redundant processing to the spiced image signals. The external monitor receives the images performed with redundant processing and then performs removal redundant processing to the images, thus effectively ensuring that pictures of the external monitor are consecutive and complete.

The present disclosure may be further arranged so that when a packet loss rate of data transmission between the image processing module and the external monitor is greater than a preset packet loss rate threshold or a bit error rate is greater than a preset bit error rate threshold, it is determined that the image signal transmission between the image processing module and the external monitor is abnormal.

According to the foregoing technical solution, the quality of the data transmission between the image processing module and the external monitor can be stably monitored, so as to ensure normal data transmission between the image processing module and the external monitor.

In view of the above, beneficial technical effects of the present disclosure may be that:
1. an effect of ensuring the system to normally output images is achieved through the setting of the signal forwarding module;
2. there is an advantage of instantly storing image data through the setting of the image caching module; and
3. an effect of effectively ensuring that the pictures displayed by the external monitor are consecutive and complete is achieved through the setting of the signal caching module.

IN THE FIGURES

- 10 Camera Module
- 11 External Monitor
- 20 Image Processing Module
- 21 White Balance Adjustment Unit
- 22 Brightness Adjustment Unit
- 23 Wide Dynamic Functional Unit
- 24 Dark Place Correction Unit
- 25 Exposure Correction Unit
- 26 Smoke Eliminating Unit
- 27 Vessel Enhancement Unit
- 28 Special Camera Unit
- 30 Front Panel Function Switching Module
- 40 Front Panel Control Module
- 50 Signal Forwarding Module
- 60 Image Caching Module
- 61 External Storage Device
- 62 USB Storage Module
- 70 Monitoring Module
- 80 Triggering Module
- 90 Signal Caching Module
- 91 Storage Unit
- 92 Numbering Unit
- 93 Eliminating Unit
- 94 Transmission Unit

DESCRIPTION

The present disclosure is further described in detail below with reference to the accompanying drawings.

Embodiment I

Figure 1:
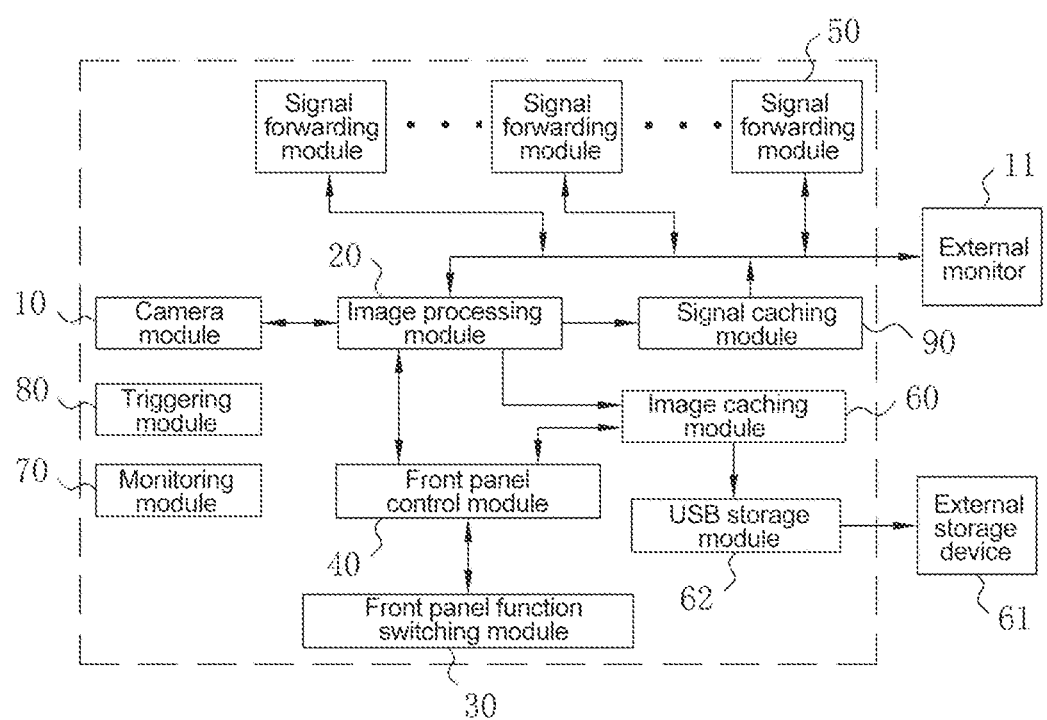
FIG. 1 is a structural block diagram of an endoscope camera system shown according to embodiment I of the present disclosure.

With reference to FIG. 1, FIG. 1 is an endoscope camera system according to the present disclosure, including a camera module 10, an image processing module 20, a front panel function switching module 30, a front panel control module 40, and a plurality of signal forwarding modules 50. The camera module 10 is configured to convert an optical signal collected by a camera to an electrical signal, and process the electrical signal as an image signal and then output the same to the image processing module 20. The image processing module 20 is connected to the camera module 10, and is configured to reprocess the image signal output by the camera module 10 and then output the same to an external monitor 11 to which the endoscope camera system is connected. The front panel control module 40 is connected to the image processing module 20 and the front panel function switching module 30, and is configured to enable the front panel function switching module 30 to communicate with the image processing module 20. The front panel function switching module 30 is configured to be operated by a user and to send a control signal for switching image processing functions to the image processing module 20 by using the front panel control module 40 based on an operation of the user.

With reference to FIG. 1, each of the signal forwarding modules 50 is directly connected to a line through which the image processing module 20 and the external monitor 11 are connected. When image signal transmission between the external monitor 11 and the image processing module 20 is abnormal, a signal forwarding module m is configured as a signal forwarding station that is used for bridging the image signal transmission between the image processing module 20 and the external monitor 11, and the signal forwarding module m is any one of the plurality of signal forwarding modules 50. It should be noted that in this embodiment, when the image signal transmission between the external monitor 11 and the image processing module 20 is abnormal, the system firstly configures the signal forwarding module 50 that is closest to the image processing module 20 as a signal forwarding station. When the image signal transmission between the external monitor 11 and the image processing module 20 is still abnormal, the system may continue to successively configure the signal forwarding modules 50 that are used for bridging the image signal transmission between the image processing module 20 and the external monitor 11 in a sequence from being closest to the image processing module 20 to being farthest away from the image processing module 20, until the image signal transmission between the external monitor 11 and the image processing module 20 is normal.

With reference to FIG. 1, the endoscope camera system further includes an image caching module 60 connected to the image processing module 20. The image caching module 60 is connected with a USB Storage Module 62. The USB Storage Module 62 is used for connecting an external storage device 61. When the system works normally, the image processing module 20 inputs an image that needs to be temporarily stored to the image caching module 60 while transmitting the image signal to the external monitor 11. When the USB Storage Module 62 is connected with an external storage device 61, the image caching module 60 may output the temporarily stored image to the external storage device 61.

With reference to FIG. 1, the endoscope camera system further includes a monitoring module 70 and a triggering module 80. When the system works normally, the monitoring module 70 may detect quality of the image signal transmission between the image processing module 20 and the external monitor 11. When the monitoring module 70 detects that the image signal transmission between the external monitor 11 and the image processing module 20 is abnormal, the triggering module 80 may control the image processing module 20 to send a start instruction to the signal forwarding module m. In this case, the signal forwarding module 50 is configured as a signal forwarding station that is used for bridging the image signal transmission between the image processing module 20 and the external monitor 11.

With reference to FIG. 1, when the system works normally, the monitoring module 70 may continuously send normal data to the external monitor 11, and the external monitor 11 sends feedback information to the monitoring module 70 after receiving the normal data. When the monitoring module 70 does not receive the corresponding feedback information, it indicates that the image signal transmission between the external monitor 11 and the image processing module 20 is abnormal at this time, and the system may start the triggering module 80 immediately. The external monitor 11 may further analyze the image signal after receiving the image signal. When the external monitor 11 analyzes that the received image signal is a distorted signal, the external monitor 11 sends warning information to the monitoring module 70. When the monitoring module 70 receives the warning information, it also indicates that the image signal transmission between the external monitor 11 and the image processing module 20 is abnormal at this time, and the system may start the triggering module 80 immediately.

Figure 2:
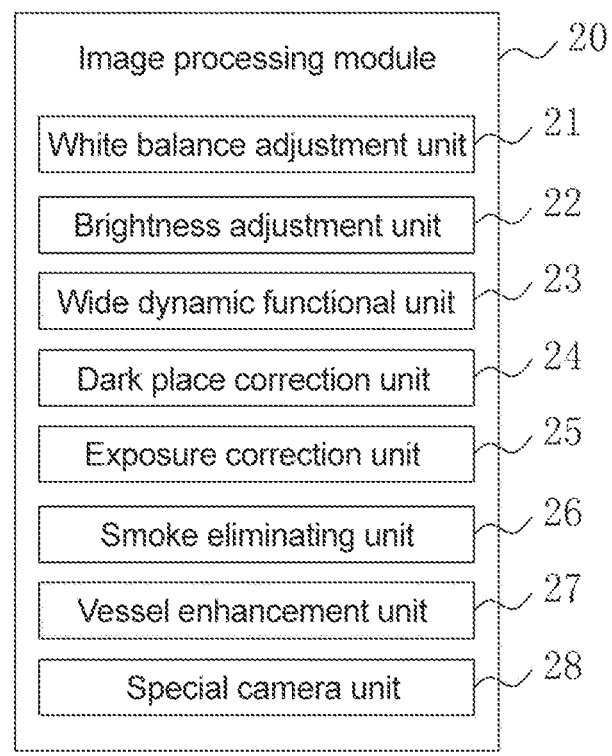
FIG. 2 is a structural block diagram of an image processing module shown according to embodiment I of the present disclosure.

With reference to FIG. 1 and FIG. 2, the image processing module 20 includes a white balance adjustment unit 21, a brightness adjustment unit 22, a wide dynamic functional unit 23, a dark place correction unit 24, an exposure correction unit 25, a smoke eliminating unit 26, a vessel enhancement unit 27, and a special camera unit 28. The white balance adjustment unit 21 is configured to adjust white balance of an output image; the brightness adjustment unit 22 is configured to adjust image brightness; the wide dynamic functional unit 23 has a function of dynamically expanding a range; the dark place correction unit 24 is configured to improve brightness at a dark place of the image; the exposure correction unit 25 can reduce excessive exposure; the smoke eliminating unit 26 can eliminate smoke generated due to an operation in the image; the vessel enhancement unit 27 can enhance color of a vessel in the image; and the special camera unit 28 is configured to perform special imaging such as monochrome. Correspondingly, the front panel function switching module 30 is provided with several function buttons that correspond to various functional units in the image processing module 20, and the user can switch corresponding functions by using the function buttons.

Figure 3:
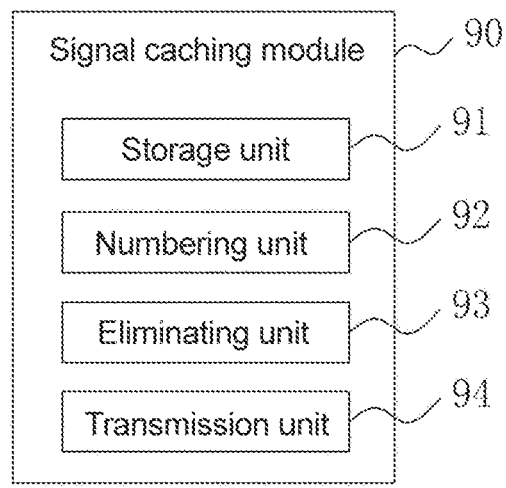
FIG. 3 is a structural block diagram of a signal caching module shown according to embodiment I of the present disclosure.

With reference to FIG. 1 and FIG. 3, the endoscope camera system further includes a signal caching module 90 connected to the image processing module 20, and the signal caching module 90 includes a storage unit 91, a numbering unit 92, an eliminating unit 93, and a transmission unit 94. The image processing module 20 synchronously sends a same image signal to the storage unit 91 and the external monitor 11.

Figure 4:
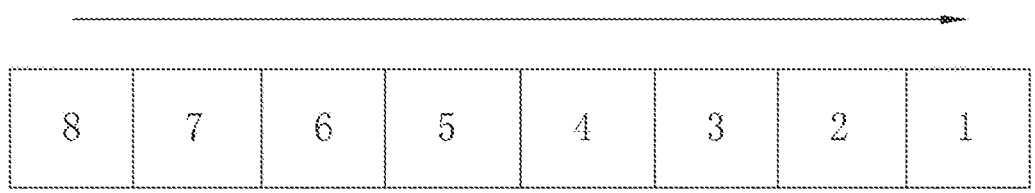
FIG. 4 is a structural block diagram displaying each storage regions in a storage unit shown according to embodiment I of the present disclosure.

With reference to FIG. 3 and FIG. 4, the storage unit 91 includes several consecutive storage regions that are used for storing the image signal. The numbering unit 92 is configured to sequentially number the storage regions in the storage unit 91. The numbering unit 92 is further configured to continuously move, when a storage region with a certain number is filled with image signals, the image signals in the storage region to a storage region with a previous number. When a storage region with a smallest number in the storage unit 91 is filled with image signals, the eliminating unit 93 is configured to eliminate the image signals in the storage region. The transmission unit 94 is configured to copy, after the signal forwarding module m is started, the image signal in the storage unit 91 and transmit the copied image signal to the signal forwarding module m.

With reference to FIG. 3 and FIG. 4, the image processing module 20 (with reference to FIG. 1) continuously transmits image signal to a storage region with a largest number in the storage unit 91, and the signal forwarding module m splices the image signal transmitted by the transmission unit 94 and the image signal transmitted by the image processing module 20 and then transmits the same to the external monitor 11 (with reference to FIG. 1). Specifically, after receiving the image signal transmitted by the transmission unit 94 and the image signal transmitted by the image processing module 20, the signal forwarding module m may splice the received image signal that is transmitted by the transmission unit 94 into the image signal transmitted by the image processing module 20, and then transmits the same to the external monitor 11 after performing redundant processing, to enable the external monitor 11 to output an image normally.

The implementation principle of the foregoing embodiments is that:

When the system works normally, the image processing module 20 continuously transmits the processed image signal to the external monitor 11, and the user can switch corresponding functions by using the function buttons on the front panel function switching module 30.

When the image signal transmission between the external monitor 11 and the image processing module 20 is abnormal, the system may configure the signal forwarding module m as a signal forwarding station, to bridge the image signal transmission between the image processing module 20 and the external monitor 11. Meanwhile, the signal caching module 90 may also copy the image signal in the storage unit 91 and transmits the copied image signal to the signal forwarding module m. The signal forwarding module m splices the image signal transmitted by the transmission unit 94 and the image signal transmitted by the image processing module 20 and then transmits the same to the external monitor 11, thus effectively ensuring a normal image output of the external monitor 11.

Embodiment II

Figure 5:
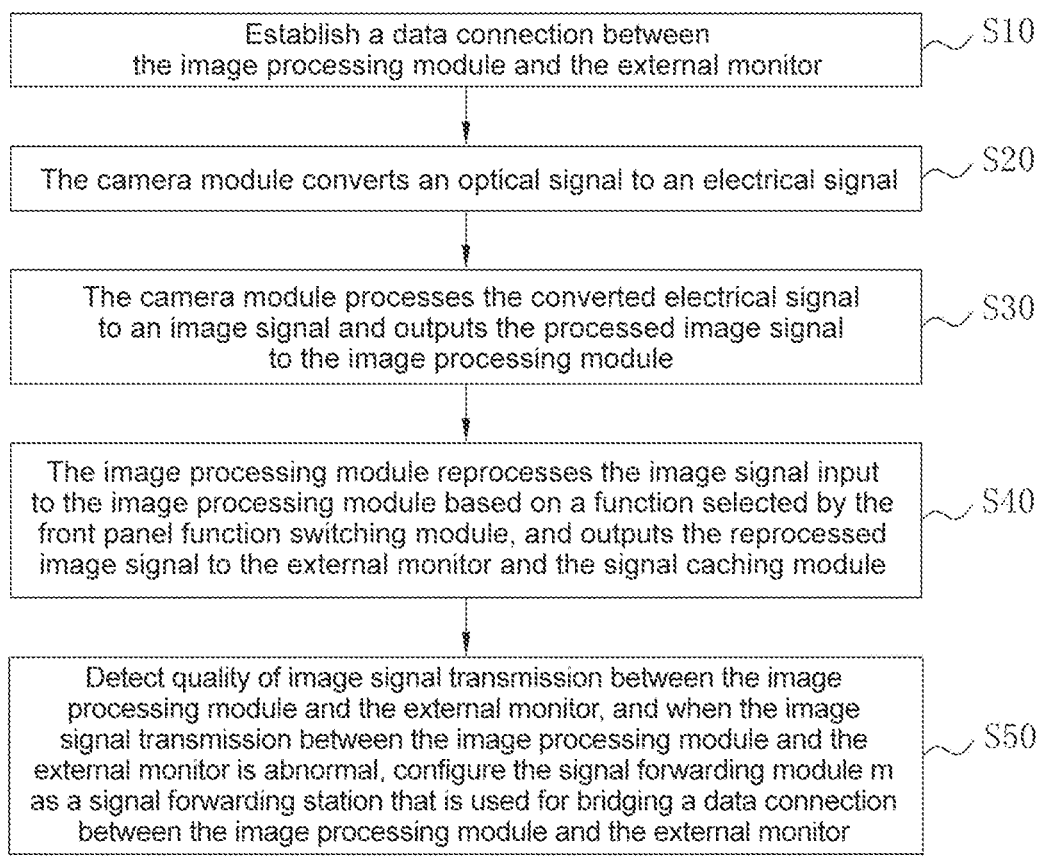
FIG. 5 is a flowchart of an image signal transmission method for an endoscope camera system shown according to embodiment II of the present disclosure.

An image signal transmission method for an endoscope camera system that is based on the endoscope camera system in embodiment I is provided. With reference to FIG. 1 and FIG. 5, the following steps may be included.

S10. Establish a data connection between the image processing module 20 and the external monitor 11.

S20. The camera module 10 converts an optical signal to an electrical signal.

S30. The camera module 10 processes the converted electrical signal as an image signal and outputs the processed image signal to the image processing module 20.

S40. The image processing module 20 reprocesses the image signal input to the image processing module 20 based on a function selected by the front panel function switching module 30, and outputs the reprocessed image signal to the external monitor 11 and the signal caching module 90.

S50. Detect the quality of the image signal transmission between the image processing module 20 and the external monitor 11, and when the image signal transmission between the image processing module 20 and the external monitor 11 is abnormal, configure the signal forwarding module m as a signal forwarding station that is used for bridging a data connection between the image processing module 20 and the external monitor 11, where the signal forwarding module m is any one of the plurality of signal forwarding modules 50.

It should be noted that when the system works normally, the monitoring module 70 may continuously send normal data to the external monitor 11, and the external monitor 11 sends feedback information to the monitoring module 70 after receiving the normal data. When a packet loss rate of data transmission between the image processing module 20 and the external monitor 11 is greater than a preset packet loss rate threshold or a bit error rate is greater than a preset bit error rate threshold, it is determined that the image signal transmission between the image processing module 20 and the external monitor 11 is abnormal. The external monitor 11 may further analyze the image signal after receiving the image signal. When the external monitor 11 analyzes that the received image signal is a distorted signal, the external monitor 11 sends warning information to the monitoring module 70. When the monitoring module 70 receives the warning information, it also indicates that the image signal transmission between the image processing module 20 and the external monitor 11 is abnormal at this time.

Figure 6:
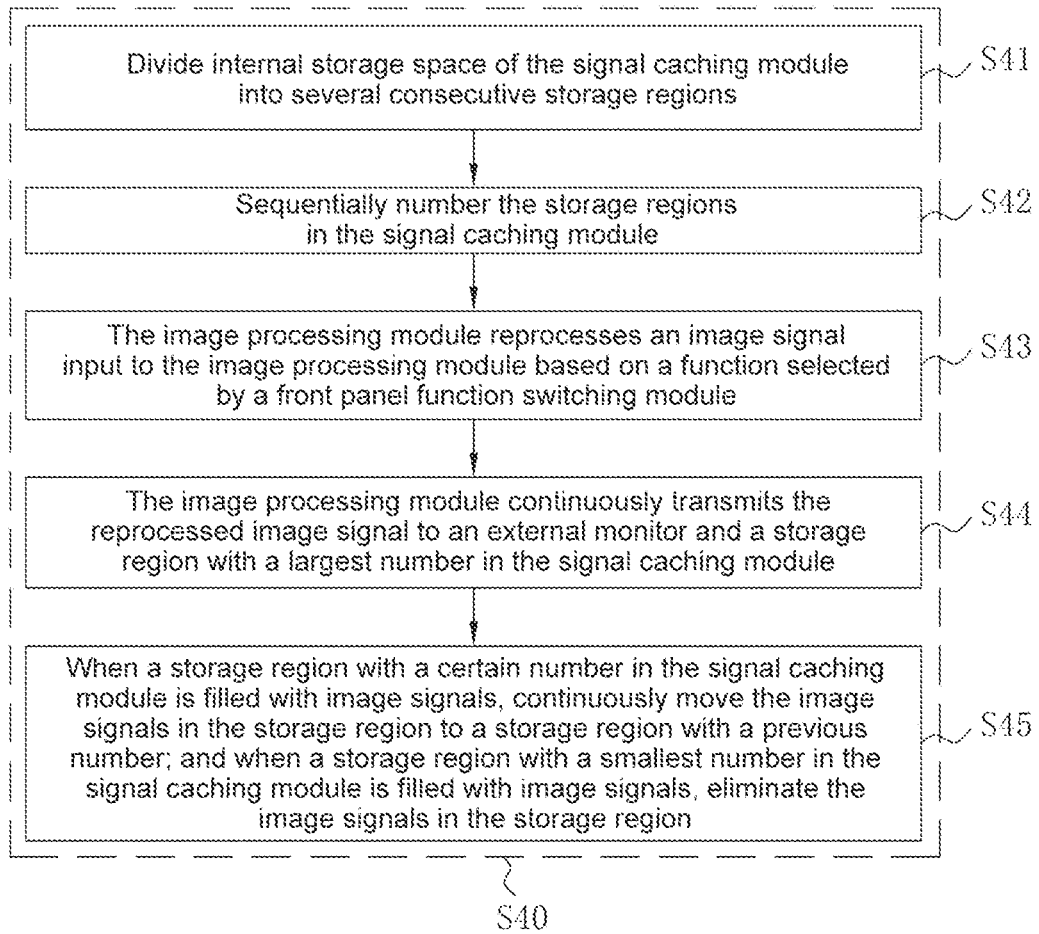
FIG. 6 is a flowchart of step S40 shown according to embodiment II of the present disclosure.

With reference to FIG. 1 and FIG. 6, the step S40 includes the following sub-steps.

S41. Divide internal storage space of the signal caching module 90 into several consecutive storage regions.

S42. Sequentially number the storage regions in the signal caching module 90.

S43. The image processing module 20 reprocesses the image signal input to the image processing module 20 based on the function selected by the front panel function switching module 30. Specifically, the front panel function switching module 30 is provided with several function buttons that correspond to each functional units in the image processing module 20, and the user can switch corresponding functions by using the function buttons.

S44. The image processing module 20 continuously transmits the reprocessed image signal to the external monitor 11 and a storage region with a largest number in the signal caching module 90.

S45. When a storage region with a certain number in the signal caching module 90 is filled with image signal, continuously move the image signal in the storage region to a storage region with a previous number; and when a storage region with a smallest number in the signal caching module 90 is filled with image signal, eliminate the image signal in the storage region.

Figure 7:
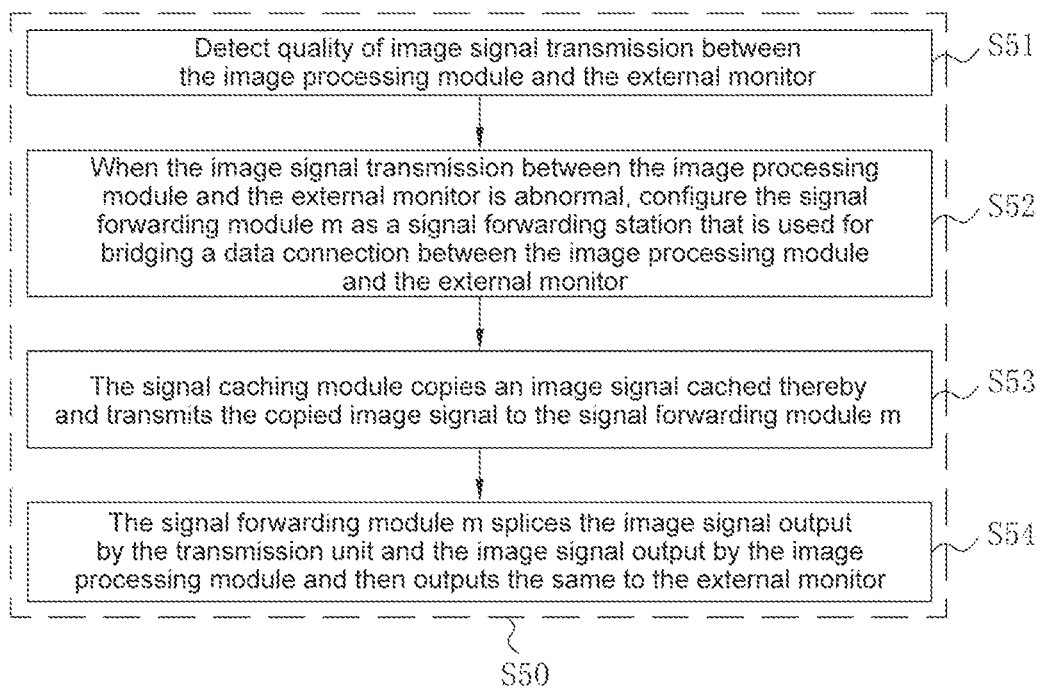
FIG. 7 is a flowchart of step S50 shown according to embodiment II of the present disclosure.

With reference to FIG. 7, the step S50 includes the following sub-steps.

S51. Detect the quality of the image signal transmission between the image processing module 20 and the external monitor 11.

S52. When the image signal transmission between the image processing module 20 and the external monitor 11 is abnormal, configure the signal forwarding module m as a signal forwarding station that is used for bridging a data connection between the image processing module 20 and the external monitor 11.

S53. The signal caching module 90 copies an image signal cached thereby and transmits the copied image signal to the signal forwarding module m.

S54. The signal forwarding module m splices the image signal output by the signal caching module 90 and the image signal output by the image processing module 20 and then outputs the same to the external monitor 11. Specifically, after receiving the image signal transmitted by the signal caching module 90 and the image signal transmitted by the image processing module 20, the signal forwarding module m may splice the received image signal that is transmitted by the signal caching module 90 into the image signal transmitted by the image processing module 20, and then transmits the same to the external monitor 11 after performing redundant processing, to enable the external monitor 11 to output an image normally.

All embodiments of this specific implementation are preferred examples of the present invention, and the protection scope of the present invention is not limited thereto. Therefore, all equivalent changes made in accordance with the structure, the shape, and the principle of the present invention shall fall within the protection scope of the present invention.

It is to be understood that the foregoing is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "e.g.," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

What is claimed is:

1. An endoscope camera system, comprising:
    a camera module, configured to convert an optical signal to an electrical signal, and process the electrical signal as an image signal to output;
    an image processing module, connected to the camera module and configured to reprocess the image signal output by the camera module and then output the same to an external monitor;
    a front panel function switching module, configured to be operated by a user and to send a control signal for switching image processing functions to the image processing module based on an operation of the user;
    a front panel control module, connected to the image processing module and the front panel function switching module, and configured to enable the front panel function switching module to communicate with the image processing module; and
    a plurality of signal forwarding modules, each of the signal forwarding modules being directly connected to a line through which the image processing module and the external monitor are connected, wherein
    when image signal transmission between the external monitor and the image processing module is abnormal, a signal forwarding module m is configured as a signal forwarding station that is used for bridging the image signal transmission between the image processing module and the external monitor, and the signal forwarding module m is any one of the plurality of signal forwarding modules.

2. The endoscope camera system according to claim 1, wherein the image processing module comprises a white balance adjustment unit, a brightness adjustment unit, a wide dynamic functional unit, a dark place correction unit, an exposure correction unit, a smoke removing unit, a vessel enhancement unit, and a special camera unit.

3. The endoscope camera system according to claim 1, wherein the endoscope camera system further comprises an image caching module connected to the image processing module, and the image caching module is configured to temporarily store an image input by the image processing module and output the temporarily stored image to an external storage device that is already connected.

4. The endoscope camera system according to claim 1, wherein the endoscope camera system further comprises:
    a monitoring module, configured to detect quality of the image signal transmission between the image processing module and the external monitor; and
    a triggering module, configured to control the image processing module to send a start instruction to the signal forwarding module m when the monitoring module detects that the image signal transmission between the external monitor and the image processing module is abnormal.

5. The endoscope camera system according to claim 4, wherein the endoscope camera system further comprises a signal caching module connected to the image processing module, and the signal caching module comprises:
    a storage unit, wherein the image processing module synchronously sends a same image signal to the storage unit and the external monitor, and the storage unit comprises several consecutive storage regions that are used for storing the image signal;
    a numbering unit, configured to sequentially number the storage regions in the storage unit, and further configured to continuously move, when a storage region with a certain number is filled with image signals, the image signals in the storage region to a storage region with a previous number;
    an eliminating unit, configured to eliminate, when a storage region with a smallest number in the storage unit is filled with image signals, the image signals in the storage region; and
    a transmission unit, configured to copy, after the signal forwarding module m is started, the image signal in the storage unit and transmit the copied image signal to the signal forwarding module m, wherein
    the image processing module continuously transmits image signals to a storage region with a largest number in the storage unit, and the signal forwarding module m splices the image signal transmitted by the transmission unit and the image signal transmitted by the image processing module and then transmits the same to the external monitor.

6. The endoscope camera system according to claim 5, wherein the monitoring module is configured to send normal data to the external monitor, the external monitor sends feedback information to the monitoring module after receiving the normal data, and the external monitor is further configured to send warning information to the monitoring module when the image signal received by the external monitor is distorted, wherein
    the triggering module is started if the monitoring module does not receive the corresponding feedback information or receives the warning information.

7. An image signal transmission method for an endoscope camera system, wherein the image signal transmission method is based on the endoscope camera system according to claim 5, and comprises the following steps:
    S10. establishing a data connection between the image processing module and the external monitor;
    S20. converting, by the camera module, an optical signal to an electrical signal;
    S30. processing, by the camera module, the converted electrical signal as an image signal and outputting the processed image signal to the image processing module;
    S40. reprocessing, by the image processing module, the image signal input to the image processing module based on a function selected by the front panel function switching module, and outputting the reprocessed image signal to the external monitor and the signal caching module; and S50. detecting the quality of the image signal transmission between the image processing module and the external monitor, and when the image signal transmission between the image processing module and the external monitor is abnormal, configuring the signal forwarding module m as a signal forwarding station that is used for bridging a data connection between the image processing module and the external monitor, wherein the signal forwarding module m is any one of the plurality of signal forwarding modules.

8. The image signal transmission method for an endoscope camera system according to claim 7, wherein the step S40 comprises the following sub-steps:

S41. dividing internal storage space of the signal caching module into several consecutive storage regions;

S42. sequentially numbering the storage regions in the signal caching module;

S43. reprocessing, by the image processing module, the image signal input to the image processing module based on the function selected by the front panel function switching module;

S44. continuously transmitting, by the image processing module, the reprocessed image signal to the external monitor and a storage region with a largest number in the signal caching module; and S45. when a storage region with a certain number in the signal caching module is filled with image signals, continuously moving the image signals in the storage region to a storage region with a previous number, and when a storage region with a smallest number in the signal caching module is filled with image signals, eliminating the image signals in the storage region.

9. The image signal transmission method for an endoscope camera system according to claim 7, wherein the step S50 comprises the following sub-steps:

S51. detecting the quality of the image signal transmission between the image processing module and the external monitor;

S52. when the image signal transmission between the image processing module and the external monitor is abnormal, configuring the signal forwarding module m as a signal forwarding station that is used for bridging a data connection between the image processing module and the external monitor;

S53. copying, by the signal caching module, an image signal cached thereby and outputting the copied image signal to the signal forwarding module m; and S54. splicing, by the signal forwarding module m, the image signal output by the signal caching module and the image signal output by the image processing module and then outputting the same to the external monitor.

10. The image signal transmission method for an endoscope camera system according to claim 7, wherein when a packet loss rate of data transmission between the image processing module and the external monitor is greater than a preset packet loss rate threshold or a bit error rate is greater than a preset bit error rate threshold, it is determined that the image signal transmission between the image processing module and the external monitor is abnormal.

* * * * *